(12) United States Patent
Lin et al.

(10) Patent No.: US 10,175,238 B2
(45) Date of Patent: Jan. 8, 2019

(54) MARKERS FOR ABNORMAL CELLS

(71) Applicant: Georgetown University, Washington, DC (US)

(72) Inventors: Chen-Yong Lin, Falls Church, VA (US); Michael D. Johnson, Rockville, MD (US); Feng-Pai Chou, Kaohsiung (TW)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/710,949

(22) Filed: May 13, 2015

(65) Prior Publication Data
US 2015/0338409 A1 Nov. 26, 2015

Related U.S. Application Data

(60) Provisional application No. 61/992,450, filed on May 13, 2014.

(51) Int. Cl.
*C12Q 1/37* (2006.01)
*G01N 33/573* (2006.01)
*G01N 33/574* (2006.01)

(52) U.S. Cl.
CPC .............. *G01N 33/573* (2013.01); *C12Q 1/37* (2013.01); *G01N 33/57426* (2013.01); *G01N 2333/96433* (2013.01); *G01N 2800/52* (2013.01)

(58) Field of Classification Search
None
See application file for complete search history.

(56) References Cited

U.S. PATENT DOCUMENTS

| 5,482,848 | A | 1/1996 | Dickson et al. |
| 7,355,015 | B1 | 4/2008 | Dickson et al. |
| 2005/0181465 | A1* | 8/2005 | Sanders ........................ 435/34 |

FOREIGN PATENT DOCUMENTS

| WO | WO2001/97794 | * 12/2001 |
| WO | WO2011063127 | * 5/2011 |

OTHER PUBLICATIONS

The International Myeloma Working Group (British Journal of Haematology, 2003, vol. 121, pp. 749-757).*
Chou (Expression, Regulation and Inhibition of Matriptase in Human B-cell Neoplasms, In : Dissertation Abstracts International, 2012, vol. 74, No. 2, Suppl. B, 218, p. 2012).*
Lee et al (Am J Physiol, 2007, vol. 293, pp. C95-C105).*
Sirard et al (Blood, 1996, vol. 87, pp. 1539-1548).*
Wang et al, Am J Physiol Cell Physiol, 2009, vol. 297, pp. C459-C470.*
Inouye et al, Journal of Biochemistry, 2010, vol. 147, pp. 485-492.*
Ding et al, Human Pathology, 2009, vol. 40, pp. 381-389.*
Beliveau et al., "Probing the substrate specificities of matriptase, matriptase-2, hepsin and DESC1 with internally quenched fluorescent peptides," FEBS Journal, 276(8):2213-2226 (2009).
Chen et al., "Antithrombin regulates matriptase activity involved in plasmin generation, syndecan shedding, and HGF activation in keratinocytes," PLoS One, 13;8(5):e62826 (2013).
Chou et al., "Imbalanced matriptase pericellular proteolysis contributes to the pathogenesis of malignant B-cell lymphomas," American Journal of Pathology, 183(4)1306-1317 (2013).
Lee et al., "Autoactivation of matriptase in vitro: requirement for biomembrane and LDL receptor domain," Am. J. Physiol. Cell Physiol., 293:C95-C105 (2007).
Mignatti et al., "Biology and biochemistry of proteinases in tumor invasion," Physiol Rev., 73(1):161-195 (1993).
Shimomura et al., "Hepatocyte growth factor activator inhibitor, a novel Kunitz-type serine protease inhibitor," J. Biol. Chem., 272(10):6370-6376 (1997).
Takeuchi et al. "Cellular localization of membrane-type serine protease 1 and identification of protease-activated receptor-2 and single-chain urokinase-type plasminogen activator as substrates," J. Biol. Chem., 275(34):26333-26342 (2000).
Tseng et al., "Matriptase activation, an early cellular response to acidosis," J. Biol. Chem., 285:3261-3270 (2010).
UniProt Accession No. Q9Y5Y6 (May 1, 2000).

* cited by examiner

*Primary Examiner* — Karen A. Canella
(74) *Attorney, Agent, or Firm* — Todd B. Buck; Haug Partners LLP (57) ABSTRACT

The present invention relates to methods of determining the presence or absence of abnormal lymphoid cells or abnormal myeloid cells in a cell sample, with the methods comprising subjecting the cell sample to conditions that will activate any inactive matriptase present in the cell sample and measuring the levels of activated matriptase in the cell sample. Once measured, these levels can then be compared to control levels of active matriptase to determine if the cell sample has elevated levels of activated matriptase over control levels of active matriptase. An elevation in the levels of activated matriptase in the cell sample is indicative that the cell sample contains abnormal lymphoid cells or abnormal myeloid cells.

23 Claims, 6 Drawing Sheets

MARKERS FOR ABNORMAL CELLS

STATEMENT REGARDING FEDERALLY SPONSORED RESEARCH OR DEVELOPMENT

Part of the work performed during development of this invention utilized U.S. Government funds under National Institutes of Health Grant No. 1R01CA123223-01A2. The U.S. Government has certain rights in this invention.

SEQUENCE LISTING INFORMATION

N/A

BACKGROUND OF THE INVENTION

Field of the Invention

The present invention relates to methods of determining the presence or absence of abnormal lymphoid cells or abnormal myeloid cells in a cell sample, with the methods comprising subjecting the cell sample to conditions that will activate any inactive matriptase present in the cell sample and measuring the levels of activated matriptase in the cell sample.

Background of the Invention

Elevated proteolytic activity has been implicated in neoplastic progression. While the exact role(s) of proteolytic enzymes in the progression of tumor remains unclear, it seems that proteases may be involved in almost every step of the development and spread of cancer. A widely proposed view is that proteases contribute to the degradation of extracellular matrix (ECM) and to tissue remodeling, and are necessary for cancer invasion and metastasis. A wide array of ECM-degrading proteases has been discovered, the expression of some of which correlates with tumor progression. These include matrix metalloproteases (MMPS) family, plasmin/urokinase type plasminogen activator system and lysosomal proteases cathepsins D and B reviewed by Mignatti et al., *Physiol. Rev.* 73: 161-95 (1993), incorporated by reference.

The strong origins of these well-characterized extracellular matrix-degrading proteases may suggest that cancer invasion is an event which either depends entirely upon stromal-epithelial cooperation or which is controlled by some other unknown epithelial-derived proteases. Matriptase was initially identified from T-47D human breast cancer cells as a major gelatinase with a migration rate between those of Gelatinase A (72-kDa, MMP-2) and Gelatinase B (92-kDa, MMP-9). It has been proposed to play a role in the metastatic invasiveness of breast cancer, e.g., see U.S. Pat. No. 5,482,848, which is incorporated herein by reference in its entirety. The primary cleavage specificity of matriptase was identified to be arginine and lysine residues, similar to the majority of serine proteases, including trypsin and plasmin. Matriptase, like trypsin, exhibits broad spectrum cleavage activity, and such activity is likely to contribute to its gelatinolytic activity. The trypsin-like activity of matriptase distinguishes it from Gelatinases A and B, which may cleave gelatin at glycin residues, the most abundant (almost one third) of amino acid residues in gelatin.

Hepatocyte growth factor (HGF) activator inhibitor-1 (HAI-1) is a Kunitz-type serine protease inhibitor which is able to inhibit HGF activator, a blood coagulation factor XII-like serine protease. The mature form of this protease inhibitor has 478 amino acid residues, with a calculated molecular mass of 53,319. A putative transmembrane domain is located at its carboxyl terminus. HAI-1 contains two Kunitz domains (domain I spans residues 246-306; domain II spans residues 371 to 431) separated by a LDL receptor domain (residues 315 to 360). The presumed P1 residue of active-site cleft is likely to be arginine-260 in Kunitz domain I and lysine 385 in domain II by alignment with bovine pancreatic trypsin inhibitor (BPTI, aprotinin) and with other Kunitz-type inhibitors. Thus, HAI-1 has specificity against trypsin-type proteases. Although HGF activator is exclusively expressed by liver cells, HAI-1 was originally purified from the conditioned media of carcinoma cells as a 40-kDa fragment doublet, rather than the proposed, mature, membrane-bound, 53-kDa form, Shimomura et al., *J. Biol. Chem.* 272: 6370-76 (1997), incorporated by reference.

SUMMARY OF THE INVENTION

The present invention relates to methods of determining the presence or absence of abnormal lymphoid cells or abnormal myeloid cells in a cell sample, with the methods comprising subjecting the cell sample to conditions that will activate any inactive matriptase present in the cell sample and measuring the levels of activated matriptase in the cell sample. Once measured, these levels can then be compared to control levels of active matriptase to determine if the cell sample has elevated levels of activated matriptase over control levels of active matriptase. An elevation in the levels of activated matriptase in the cell sample is indicative that the cell sample contains abnormal lymphoid cells or abnormal myeloid cells.

The present invention also relates to methods of monitoring the progression of a treatment for abnormal lymphoid cells or abnormal myeloid cells in a subject receiving the treatment, with the methods comprising subjecting at least two separate cell samples, taken from the subject at various time points, to conditions that will activate any inactive matriptase present in the cell sample, and measuring the levels of activated matriptase in each of the cell samples. Once measured, these levels can then be compared to one another to determine if activated matriptase is changing over time. A decline in the levels of activated matriptase over time is indicative that the treatment for the abnormal lymphoid cells or the abnormal myeloid cells is not ineffective, and an increase in the levels of activated matriptase over time is indicative that the treatment for the abnormal lymphoid cells or the abnormal myeloid cells is not effective.

The present invention also relates to methods of monitoring the progression of the development of abnormal lymphoid cells or abnormal myeloid cells in a subject, with the methods comprising subjecting at least two separate cell samples, taken from the subject at various time point, to conditions that will activate any inactive matriptase present in the cell sample, and measuring the levels of activated matriptase in each of the cell samples. Once measured, these levels are compared to one another to determine if activated matriptase is changing over time. A decline in the levels of activated matriptase over time is indicative that the levels of abnormal lymphoid cells or abnormal myeloid cells is declining in the subject, and an increase in the levels of activated matriptase over time is indicative that the levels of abnormal lymphoid cells or abnormal myeloid cells is increasing.

The present invention also relates to kits for determining the presence or absence of abnormal lymphoid cells or abnormal myeloid cells in a cell sample from a subject, the kit comprising a solution to activate inactive matriptase present in the cell sample and a substrate on which the activated matriptase will act.

DETAILED DESCRIPTION OF THE INVENTION

Figure 1:
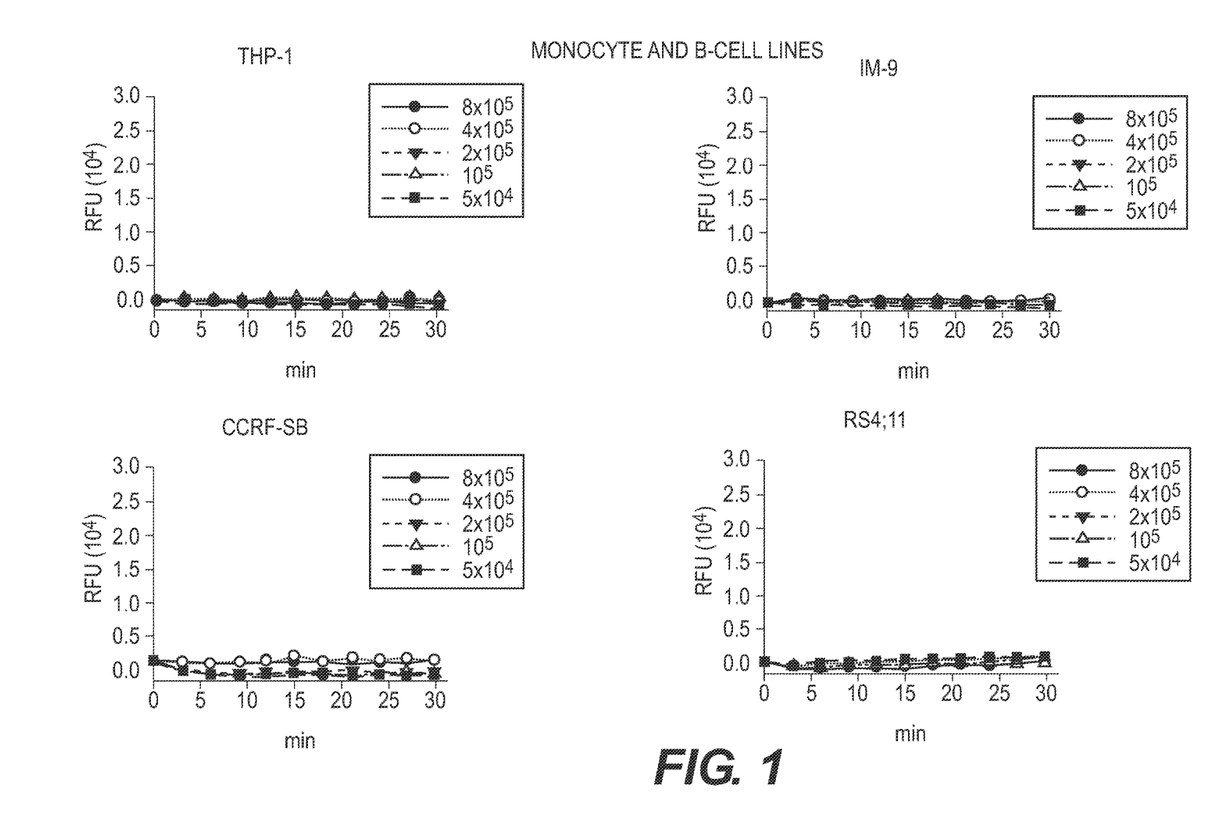
FIG. 1 depicts blood drawn from healthy individuals, with no signs or symptoms of abnormal blood conditions, exhibit low to non-existent levels of active matriptase, even spiked with abnormal lymphoid or myeloid cells that are known not to exhibit active matriptase.
Figure 2:
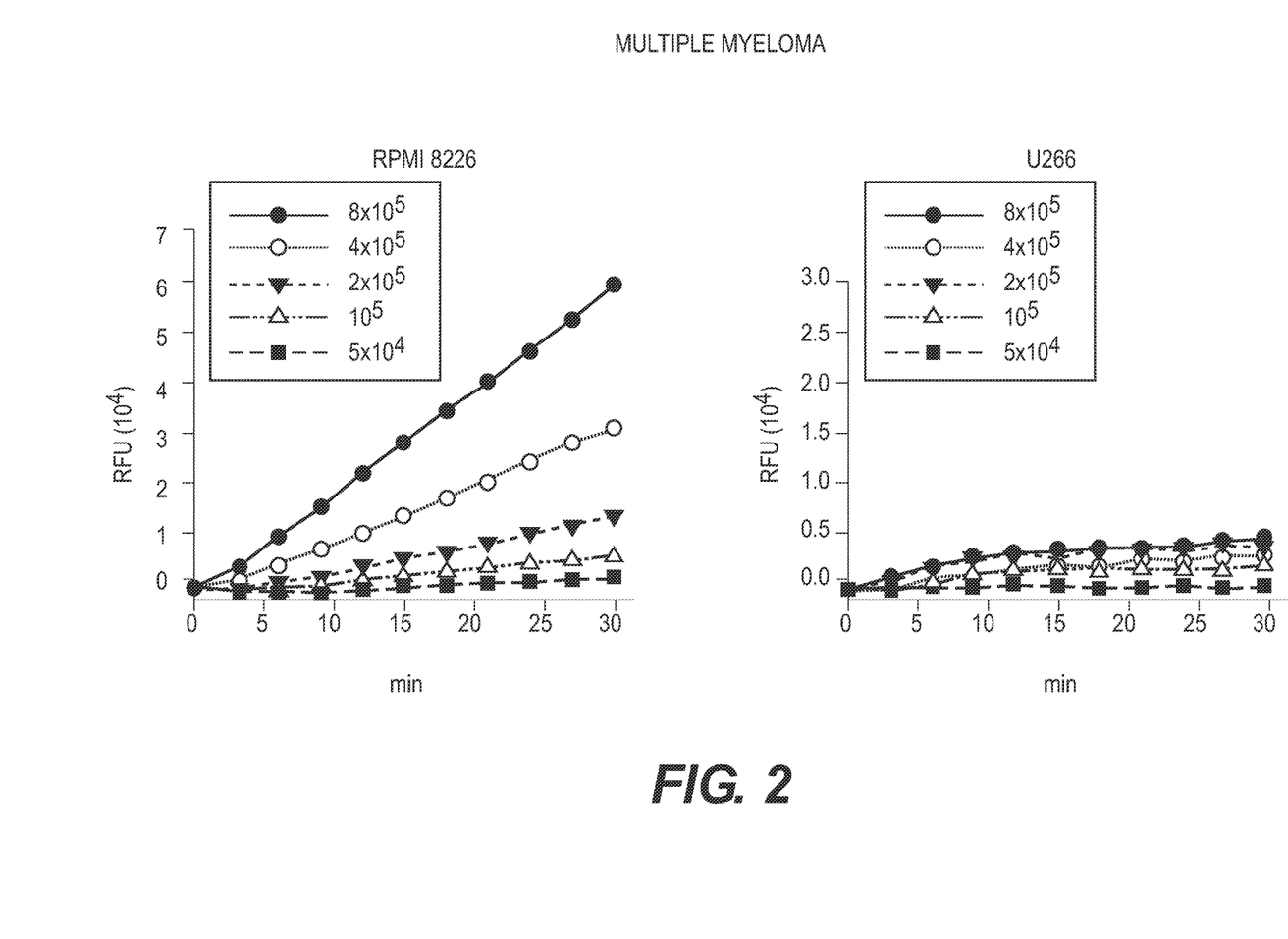
FIG. 2 depicts that blood spiked with abnormal myeloid cells (RPMI 8226 multiple myeloma) that are known to exhibit active matriptase can be detected using the methods of the present invention. Fluorescence intensity generally correlates with number of cells. Abnormal myeloid cells (U266 multiple myeloma) that are known not to exhibit active matriptase are not detectable.
Figure 3:
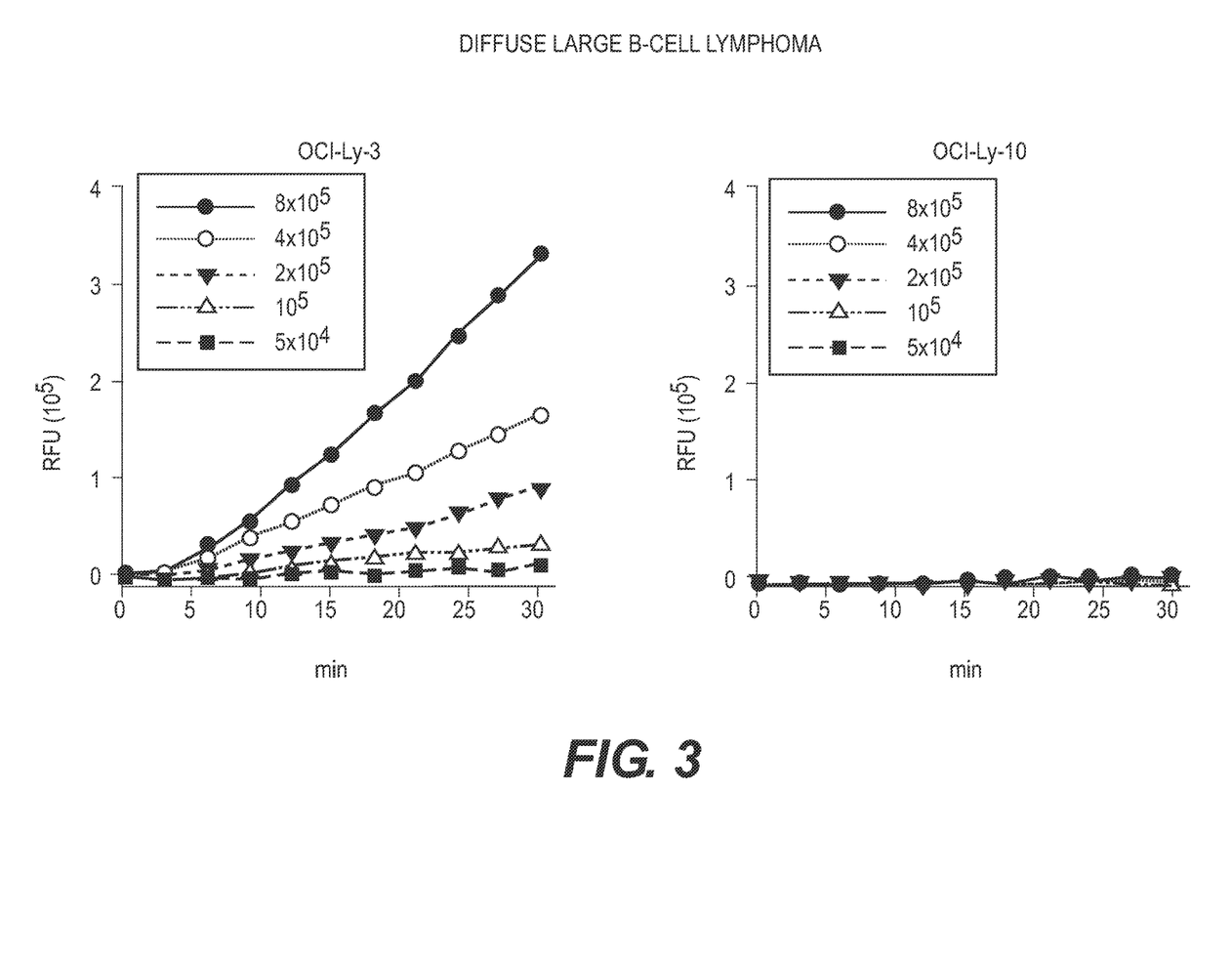
FIG. 3 depicts that blood spiked with abnormal lymphoid cells (OCI-Ly-3 Diffuse Large B-cell Lymphoma cells) that are known to exhibit active matriptase can be detected using the methods of the present invention. Fluorescence intensity generally correlates with number of cells. Abnormal lymphoid cells (OCI-Ly-10 Diffuse Large B-cell Lymphoma cells) that are known not to exhibit active matriptase are not detectable.
Figure 4:
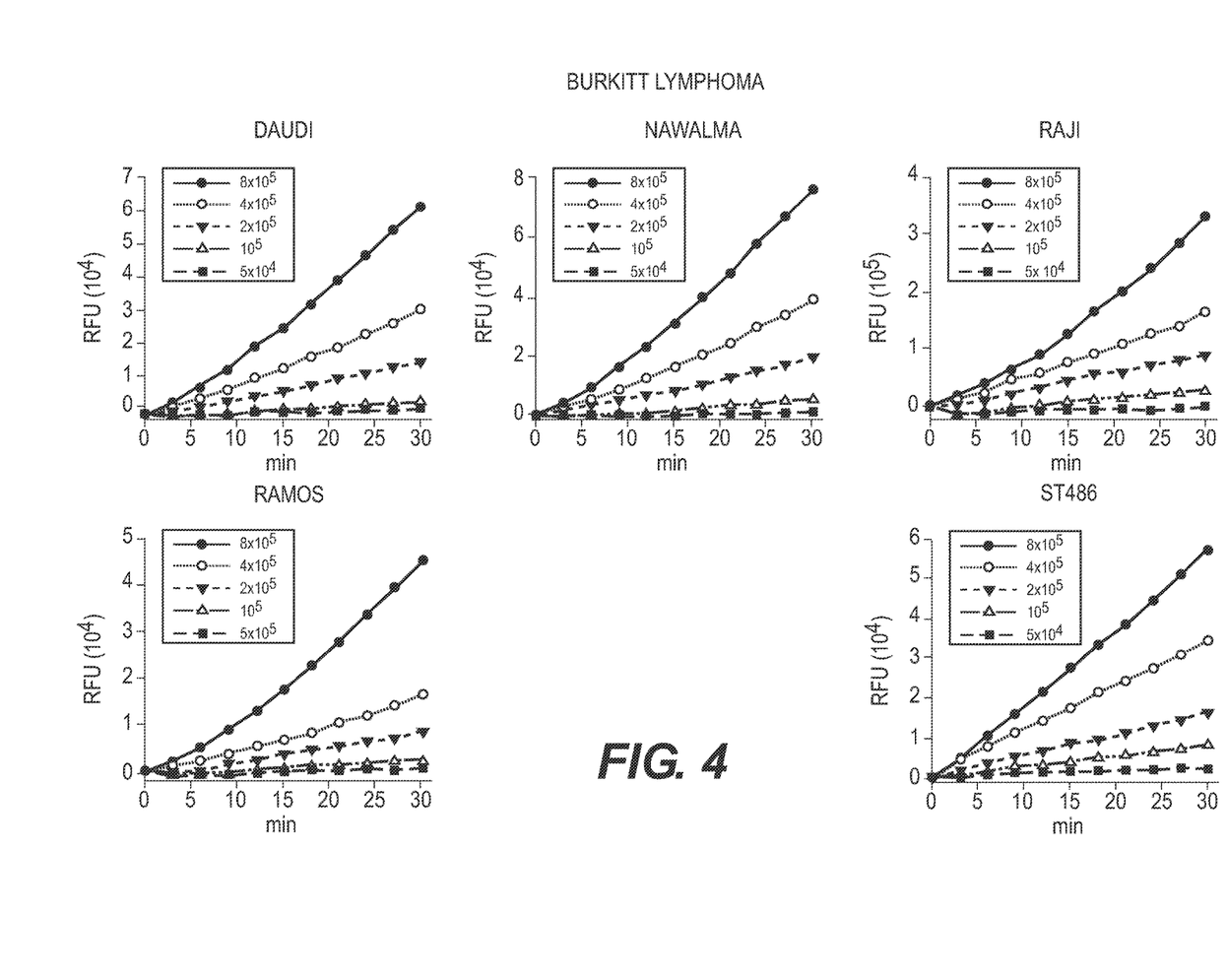
FIG. 4 depicts that blood spiked with abnormal lymphoid cells that are known to exhibit active matriptase can be detected using the methods of the present invention. Fluorescence intensity generally correlates with number of cells.
Figure 5:
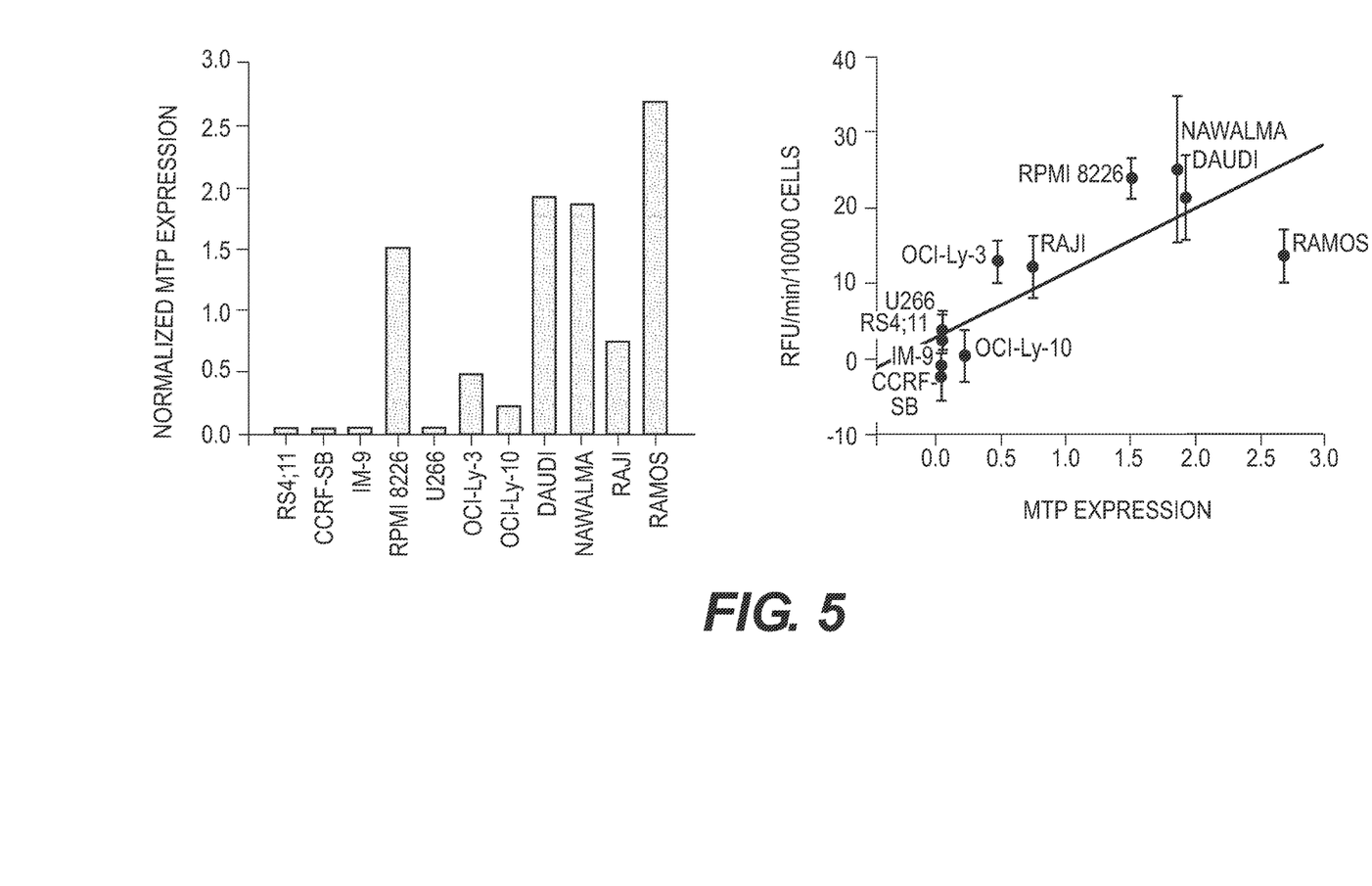
FIG. 5 depicts that the fluorescence signal generated in one embodiment of the methods of the present is generally dependent on cell number and expression levels.
Figure 6:
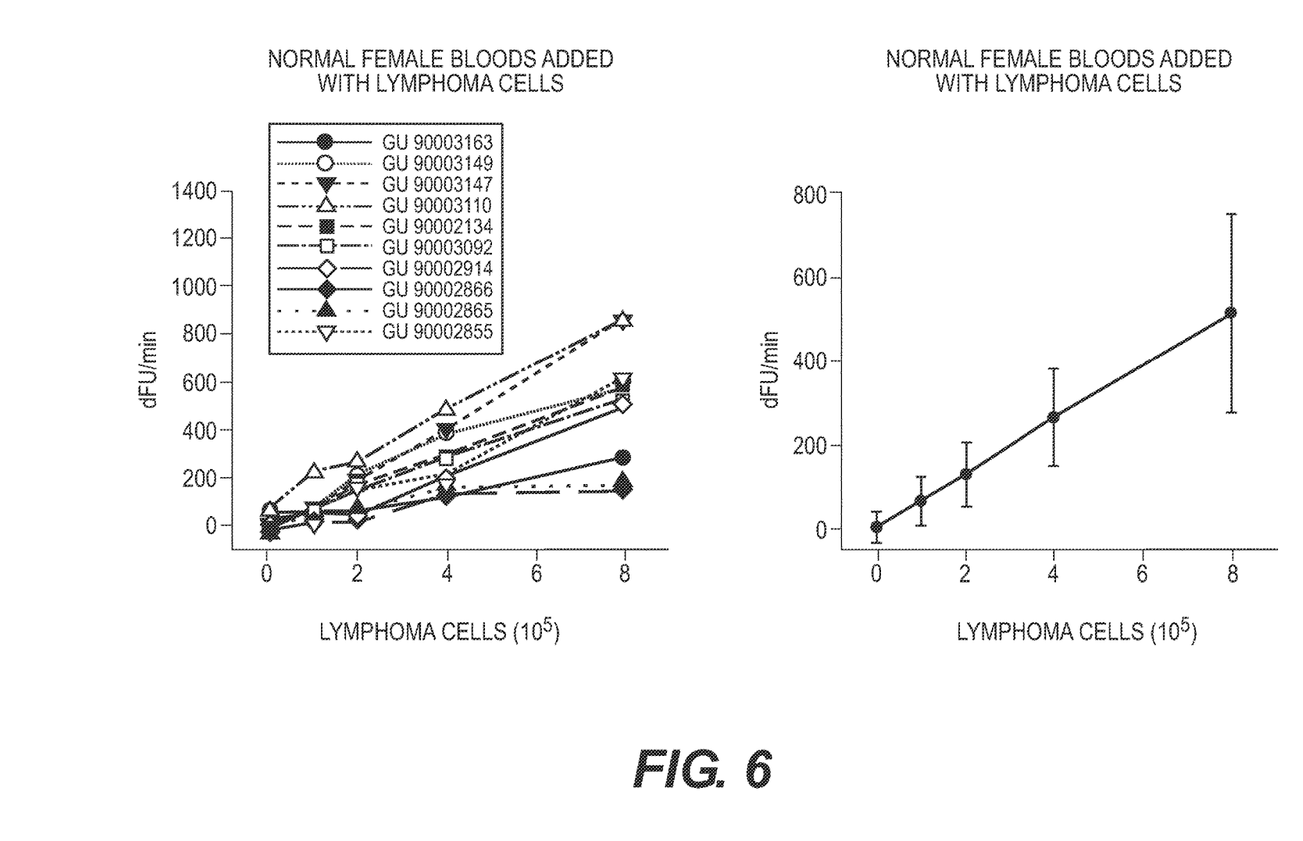
FIG. 6 depicts that, similar to the results shown in FIG. 5, the fluorescence signal generated in one embodiment of the methods of the present is generally dependent on cell number and expression levels, when the same number and type of abnormal lymphoid and abnormal myleoid cells are spiked into normal blood.

The present invention relates to methods of determining the presence or absence of abnormal lymphoid cells or abnormal myeloid cells in a cell sample, with the methods comprising subjecting the cell sample to conditions that will activate any inactive matriptase present in the cell sample and measuring the levels of activated matriptase in the cell sample.

As used herein, "lymphoid cells" is used to mean cells of lymphoid lineage, for example B cell, T cells, natural killer (NK) cells and plasma cells. Lymphoid cells include lymphoid stem cells, mature B cells and T cells, and all cell types there between, such as but not limited to Pre B cells, B lymphoblasts, prothymocytes and T lymphocytes. "Abnormal lymphoid cells" are cells of lymphoid lineage that exhibit abnormal metabolism, growth patterns, protein expression patterns, or morphology. For example, abnormal lymphoid cells may be cells of lymphoid lineage that do not undergo apoptosis at the appropriate time, or that divide more than normal. By way of another example, abnormal lymphoid cells may be cells of lymphoid lineage that do not appear to be morphologically normal to a clinician, such as a pathologist or histologist.

As used herein, "myeloid cells" is used to mean cells of myeloid lineage, in general white blood cells such as mast cells, neutrophils, eosinophils, basophils, monocytes and macrophages. Myeloid cells include myeloid stem (progenitor) cells, myoblasts, and the mature cells. "Abnormal myeloid cells" are cells of myeloid lineage that exhibit abnormal metabolism, growth patterns, protein expression patterns, or morphology. For example, abnormal myeloid cells may be cells of myeloid lineage that do not undergo apoptosis at the appropriate time, or that divide more than normal. By way of another example, abnormal myeloid cells may be cells of myeloid lineage that do not appear to be morphologically normal to a clinician, such as a pathologist or histologist.

As used herein, the phrase "condition marked by the presence of abnormal lymphoid cells or abnormal myeloid cells" is used mean a condition or disease present in a subject in which abnormal lymphoid cells or abnormal myeloid cells either cause the condition or disease or a condition in a subject in which abnormal lymphoid cells or abnormal myeloid cells are symptoms of an underlying condition. Such conditions marked by the presence of abnormal lymphoid cells or abnormal myeloid cells include but are not limited to Castleman disease, Kaposi sarcoma, Hodgkin lymphoma, leukemia, acute lymphocyctic leukemia, acute myeloid leukemia, chronic lymphocyctic leukemia, chronic myeloid leukemia, chronic myelomonocytic leukemia, lymphoma, non-Hodgkin lymphoma, thymus cancer and Waldenstrom macroglobulinemia to name a few. Within each of these conditions or diseases, there may be further subdivisions such as Burkitt's lymphoma, diffuse large B-cell lymphoma (DLBCL), mantle cell lymphoma, Sezary syndrome, aggressive NK-cell leukemia and the like.

The methods disclosed herein may require obtaining a cell sample from a subject. As used herein, the term "subject" or "test subject" indicates a mammal, in particular a human or non-human primate. The test subject may or may not be in need of an assessment of a predisposition a condition or disease present in which abnormal lymphoid cells or abnormal myeloid cells either cause the condition or disease or a condition in a subject in which abnormal lymphoid cells or abnormal myeloid cells are symptoms of an underlying condition.

Examples of sources that might be used in obtaining the cell sample from the subject include, but are not limited to, biological fluids such as but are not limited to whole blood, serum, plasma, umbilical cord blood, cerebrospinal fluid, urine, amniotic fluid, lymph fluids, and various external secretions of the respiratory, intestinal and genitourinary tracts, tears, saliva, milk, nipple aspirate fluids, mammary ductal lavage fluids, abdominal washings, bronchial lavage fluids, plural fluids, white blood cells, myelomas and the like. Test samples to be assayed also include but are not limited to tissue specimens including normal and abnormal tissue, such as but not limited to bone marrow. As used herein, a cell sample is simply a collection of fluid or tissue from the subject that contains cells.

The cell sample may or may not processed prior assaying levels of activated matriptase and/or a matriptase profile. For example, whole blood may be taken from an individual and the blood sample may be processed, e.g., centrifuged, to isolate cells, plasma or serum from the blood. The cell sample may or may not be stored, e.g., frozen, prior to processing or analysis. If the sample has a few or minimal number of cells, the cells may be isolated and then expanded in culture using standard culture techniques. Thus the methods may or may not include expanding the number of cells in the cell sample prior to performing the methods described herein.

The methods described herein comprise subjecting the cell sample to conditions that will activate any inactive matriptase present in the cell sample. Matriptase (matriptase-1) is a well-known type II transmembrane serine protease that is broadly expressed in epithelial cells and tissues. Generally, matriptase exhibits trypsin-like activity and prefers Arg or Lys at the P1 site of cleavage, and, in general prefers a small-side-chain amino acid, such Ala or Gly at the P2 position. The terms P1, P2, etc., as well as the terms P1', P2', etc are well known to those in the art. In addition, Matriptase is also known as suppressor of tumorigenicity 14 protein (ST14) and serine protease 14 and membrane-type serine protease 1 (MT-SP1). Additional information about matriptase can be found on the Uniprot database on the world wide web at www.uniprot.org under accession number Q9Y5Y6, the entirety of which is incorporated by reference.

Matriptase is generally not expressed on lymphoid or myeloid cells. To the extent that matriptase is expressed on lymphoid or myeloid cells it is normally expressed in extremely low to undetectable levels. The cognate inhibitor of matriptase is hepatocyte growth factor activator inhibitor-1 (HAI-1), also known as Kunitz-type protease inhibitor 1, and both matriptase and HAI-1 are normally co-expressed in epithelial tissues such that interactions between the matriptase protease and the surrounding epithelium can be tightly controlled and regulated. HAI-1 rapidly binds to active matriptase upon matriptase zymogen activation, followed by shedding of matriptase-HAI-1 complex. Additional information about HAI-1 can be found on the Uniprot database on the world wide web at www.uniprot.org under accession number Q43278, the entirety of which is incorporated by reference.

As disclosed above, matriptase is generally not expressed on normal lymphoid or normal myeloid cells. The inventors have discovered, however, that abnormal lymphoid or abnormal myeloid cells may express matriptase in either an active or inactive form. As used herein, the phrase "inactive matriptase" is used to mean a matriptase protein that is capable of functioning in a normal manner when the inhibition of the protein is either removed or reduced. Thus, "subjecting the cell sample to conditions that will activate inactive matriptase" or "activating inactive matriptase" (which are used interchangeably herein) includes removing or inactivating the compound or mechanism that is maintaining the matriptase in a state of inhibition. In one specific embodiment, subjecting the cell sample to conditions that will activate any inactive matriptase present in the cell sample involves subjecting the matriptase to an acidic environment, such as but not limited to a buffer with an acidic pH. In more specific embodiments, subjecting the cell sample to conditions that will activate any inactive matriptase present in the cell sample comprises the use of mildly acidic buffers, including but not limited to phosphate and citrate-phosphate buffers. In more specific embodiments, subjecting the cell sample to conditions that will activate any inactive matriptase present in the cell sample comprises the use of an acidic buffer with a pH of between about 6.9 and about 5.0. In more specific embodiments, subjecting the cell sample to conditions that will activate any inactive matriptase present in the cell sample comprises the use of an acidic buffer with a pH of between about 6.8 and about 5.2, between about 6.6 and about 5.4, between about 6.4 and about 5.6, between about 6.2 and about 5.8, between about 6.1 and about 5.9, or about 6.0. In even more specific embodiments, subjecting the cell sample to conditions that will activate any inactive matriptase present in the cell sample comprises the use of a phosphate buffered saline (PBS) with a pH of between about 6.9 and about 5.0, between about 6.8 and about 5.2, between about 6.6 and about 5.4, between about 6.4 and about 5.6, between about 6.2 and about 5.8, between about 6.1 and about 5.9, or about 6.0.

Once activated, the active matriptase can be measured. As used herein, measuring the levels of active matriptase includes direct and indirect measurements. For example, in some embodiments, the methods of the present invention include directly measuring levels of active matriptase, for example, by Western Blot analysis and gelatin zymography.

In alternative embodiments, the methods of the present invention also include indirectly measuring actived matriptase levels by, for example, measuring the activity of activate matriptase. For example, levels of active matriptase can be measured by placing a known substrate, synthetic or naturally occurring, in contact with the active matriptase and observing, measuring and/or determining at least one of the cleavage products from the action of matriptase on the substrate. As is well-known in the art, a protease enzyme will act upon a substrate, usually a protein or peptide and often times at a specifically defined location within the substrate such as between two amino acid residues, and will cleave the substrate into at least two portions. Observing, measuring and/or determining at least one of these cleavage products, therefore, is an indirect measurement of matriptase activity. In one embodiment, measuring the activity of activate matriptase includes but is not limited to placing a substrate peptide in contact with at least a portion of the cell sample that contains active matriptase to form a cell sample-substrate mixture. The matriptase in the mixture will then act on the substrate peptide and the levels of at least one of the substrate cleavage products are measured. In specific embodiments, the substrate peptide is a fluorogenic peptide. As used herein, a fluorogenic peptide is a peptide that either contains a fluorescent moiety or is naturally fluorescent. Examples, of fluorogenic peptide substrates that can be used in the methods of the present invention include but are not limited to N-tertbutoxycarbonyl-Gln-Ala-Arg-7-amido-4-methylcoumarin, and peptides containing Arg as P1 site and other chemicals that can be observed, measured and/or determined after the action of active matriptase. Any peptide sequence on which matriptase acts can generally be transformed into a fluorogenic substrate by adding moieties to the peptide that will both fluoresce and also quench fluorescence. The fluorescence quenching is removed from the vicinity of fluorescent moiety when active matriptase acts on the fluorogenic peptide, in turn, allowing the fluorescence of the fluorescent moiety to be detected.

When using fluorogenic peptides in the methods of the present invention, at least one luminescent property of the cell sample-substrate mixture will change as a result of matriptase acting on the fluorogenic substrate. Examples of luminescent properties that may change as a result of matriptase acting on the fluorogenic substrate include but are not limited to a change of the emission wavelength, intensity, lifetime, energy transfer efficiency, and/or polarization of the mixture. In one specific example, the fluorescent intensity of the cell sample-substrate mixture will change as a result of matriptase acting on the fluorogenic substrate. In a more specific embodiment, the fluorescent intensity of the cell sample-substrate mixture will decrease as a result of matriptase acting on the fluorogenic substrate. In another specific embodiment, the fluorescent intensity of the cell sample-substrate mixture will increase as a result of matriptase acting on the fluorogenic substrate.

In some embodiments, the substrate is added to at least a portion of the cell sample. The portion of the cell sample to which the substrate is added may or may not include cells. In other words, once the cells are harvested from the subject (and optionally expanded in culture prior to performing the methods of the present invention), it is not necessary that cells are present when assessing levels of activated matriptase. The activated matriptase that is measured in the assays may also include the "shed fraction" of matriptase, which includes the fraction of matriptase that cells normally shed into their local environment, e.g., blood stream, cell culture medium, etc. Thus the phrase "portion of a cell sample" as used herein may or may not include cells when the levels of active matriptase are measured, e.g., an aliquot of cell culture supernatant or cell culture medium may be used when measuring the levels of active matriptase. To be clear, a cell sample is obtained from the subject, and this cell sample may be processed after matriptase activation at a later time such that the levels of active matriptase are determined in a portion of the cell sample that does not contain cells, i.e., the portion is cell-free. Of course, the levels of active matriptase may also be determined in a portion of the cell sample that does contain cells.

In some embodiments, the substrate may be affixed onto the surface of a support. The terms "support" and "surface" refer to a solid phase which is a porous or non-porous water insoluble material that can have any of a number of shapes, such as strip, rod, particle, beads, or flat surfaces, such as but not limited to, the bottom of a cell culture dish, such as a 96-well plate.

In some embodiments, the support has a fixed organizational support matrix that may also function as an organization matrix, such as a microtiter tray (96-well plate). Support materials include, but are not limited to, cellulose, polysaccharide such as Sephadex, glass, polyacryloylmorpholide, silica, controlled pore glass (CPG), polystyrene, polystyrene/latex, polyethylene such as ultra high molecular weight polyethylene (UPE), polyamide, polyvinylidine fluoride (PVDF), polytetrafluoroethylene (PTFE; TEFLON), carboxyl modified teflon, nylon, nitrocellulose, and metals and alloys such as gold, platinum and palladium. The support can be biological, non-biological, organic, inorganic, or a combination of any of these, existing as particles, strands, precipitates, gels, sheets, pads, cards, strips, dipsticks, test strips, tubing, spheres, containers, capillaries, pads, slices, films, plates, slides, etc., depending upon the particular application. In one embodiment, the support on which the substrate is affixed is planar in shape, to facilitate contact with the portion of the cell sample containing the activated matriptase. Other suitable support materials will be readily apparent to those of skill in the art. The support can be a membrane, with or without a backing (e.g., polystyrene or polyester card backing), such as those available from Millipore Corp. (Bedford, Mass.), e.g., Hi-Flow™ Plus membrane cards. The surface of the support may contain reactive groups, such as carboxyl, amino, hydroxyl, thiol, or the like for the attachment of the substrate to the surface or support. The surfaces on the support may or may not be composed of the same material as the support itself. Thus, the surface can be composed of any of a wide variety of materials, such as polymers, plastics, resins, polysaccharides, silica or silica-based materials, carbon, metals, inorganic glasses, membranes, or any of the aforementioned support materials, e.g., as a layer or coating.

The assessment of the levels of activated matriptase and/or a matriptase profile can be expressed as absolute or relative values and may or may not be expressed in relation to another component, a standard an internal standard or another molecule of compound known to be in the sample. If the levels are assessed as relative to a standard or internal standard, the standard may be added to the test sample prior to, during or after sample processing.

Once levels of the activated matriptase are measured or assessed, either directly or indirectly, these measured levels can then be compared to control levels of active matriptase. Control levels of activate matriptase levels that are deemed to be normal levels of activated matriptase levels. To establish the measured activated matriptase levels of a normal individual, an individual or group of individuals may be first diagnosed or assessed to ensure that they do not have a condition marked by the presence of abnormal lymphoid or myeloid cells. The individual or group of individuals may also be diagnosed or assessed to ensure they do not have any other condition, disease, abnormality, even if the condition, disease or abnormality is typically not marked by the presence of abnormal lymphoid or myeloid cells. In another embodiment, normal measured activated matriptase levels or a normal matriptase profile is assessed in a sample from a different subject or patient (from the subject being analyzed) and this different subject does not have or is not suspected of having a condition marked by the presence of abnormal lymphoid or myeloid cells. In still another embodiment, the normal measured activated matriptase levels or a normal matriptase profile is assessed in a population of healthy individuals, the constituents of which display no signs of a condition marked by the presence of abnormal lymphoid or myeloid cells. Thus, the subject's measured activated matriptase levels or matriptase profile can be compared to normal measured activated matriptase levels or a normal matriptase profile generated from a single normal sample or generated from more than one normal sample.

Once "normalcy" established by whatever standards are deemed necessary, the measured activated matriptase levels of the individual or group of individuals, as well as any other data that might be included in a matriptase profile, can then be determined to establish a "normal measured activated matriptase levels" or "normal matriptase profile." In one embodiment, normal measured activated matriptase levels or a normal matriptase profile can be ascertained from the same subject when the subject is deemed to be normal as described above. In one embodiment, normal measured activated matriptase levels or a normal matriptase profile are/is assessed in the same subject from whom the sample is taken prior to the onset of any symptoms or outward signs of conditions marked by the presence of abnormal lymphoid or myeloid cells. That is, the term "normal" with respect to normal measured activated matriptase levels or a normal matriptase profile can be used to mean the subject's baseline normal measured activated matriptase levels or a normal matriptase profile prior to the onset of any symptoms or outward signs of conditions marked by the presence of abnormal lymphoid or myeloid cells. The measured activated matriptase levels or matriptase profile can then be reassessed periodically and compared to the subject's baseline measured activated matriptase levels or matriptase profile.

Of course, measurements of normal measured activated matriptase levels or a normal matriptase profile can fall within a range of values, and values that do not fall within this "normal range" are said to be outside the normal range. These measurements may or may not be converted to a value, number, factor or score as compared to measurements in the "normal range." For example, a specific measured value that is below the normal range, may be assigned a value or −1, −2, −3, etc., depending on the scoring system devised.

In another embodiment, the value assigned to the matriptase profile can be the collection of data from the individual measurements and need not be converted to a scoring system, such that a "matriptase profile value" is a collection of the individual measurements of the individual components of the profile.

The comparison of the measured activated matriptase levels to control levels is to determine if the cell sample has elevated levels of activated matriptase over control levels of active matriptase. An elevation in the levels of activated matriptase in the cell sample is indicative that the cell sample contains abnormal lymphoid cells or abnormal myeloid cells. In the alternative, an elevation in the levels of activated matriptase in the cell sample is indicative that subject from which the cell sample was taken has an increased risk of developing a condition marked by the presence of abnormal lymphoid cells or abnormal myeloid cells.

As used herein, the term means "increased risk" is used to mean that the test subject has an increased chance of developing or acquiring a condition marked by the presence of abnormal lymphoid or abnormal myeloid cells compared to a normal individual. The increased risk may be relative or absolute and may be expressed qualitatively or quantitatively. For example, an increased risk may be expressed as simply determining the subject's matriptase profile and placing the patient in an "increased risk" category, based upon previous population studies. Alternatively, a numerical expression of the subject's increased risk may be determined based upon the matriptase profile. As used herein, examples of expressions of an increased risk include but are not limited to, odds, probability, odds ratio, p-values, attributable risk, relative frequency, positive predictive value, negative predictive value, and relative risk.

For example, the correlation between a subject's matriptase profile and the likelihood of suffering from a condition marked by the presence of abnormal lymphoid or abnormal myeloid cells may be measured by an odds ratio (OR) and by the relative risk (RR). If $P(R^+)$ is the probability of developing a condition marked by the presence of abnormal lymphoid or abnormal myeloid cells for individuals with the risk profile (R) and $P(R^-)$ is the probability of developing a condition marked by the presence of abnormal lymphoid or abnormal myeloid cells for individuals without the risk profile, then the relative risk is the ratio of the two probabilities: $RR=P(R^+)/P(R^-)$.

In case-control studies, however, direct measures of the relative risk often cannot be obtained because of sampling design. The odds ratio allows for an approximation of the relative risk for low-incidence diseases and can be calculated: $OR=(F^+/(1-F^+))/(F^-/(1-F^-))$, where $F^+$ is the frequency of a risk profile in cases studies and $F^-$ is the frequency of risk profile in controls. $F^+$ and $F^-$ can be calculated using the risk profile frequencies of the study.

In one embodiment, the increased risk of a patient can be determined from p-values that are derived from association studies. Specifically, associations with specific profiles can be performed using regression analysis by regressing the matriptase profile with a condition marked by the presence of abnormal lymphoid or abnormal myeloid cells. In addition, the regression may or may not be corrected or adjusted for one or more factors. The factors for which the analyses may be adjusted include, but are not limited to, age, sex, weight, ethnicity, geographic location, fasting state, state of pregnancy or post-pregnancy, menstrual cycle, general health of the subject, alcohol or drug consumption, caffeine or nicotine intake and circadian rhythms, and the subject's genotype to name a few.

Increased risk can also be determined from p-values that are derived using logistic regression. Binomial (or binary) logistic regression is a form of regression which is used when the dependent is a dichotomy and the independents are of any type. Logistic regression can be used to predict a dependent variable on the basis of continuous and/or categorical independents and to determine the percent of variance in the dependent variable explained by the independents, to rank the relative importance of independents; to assess interaction effects, and to understand the impact of covariate control variables. Logistic regression applies maximum likelihood estimation after transforming the dependent into a "logit" variable (the natural log of the odds of the dependent occurring or not). In this way, logistic regression estimates the probability of a certain event occurring. These analyses are conducted with the program SAS.

SAS ("statistical analysis software") is a general purpose package (similar to Stata and SPSS) created by Jim Goodnight and N.C. State University colleagues. Ready-to-use procedures handle a wide range of statistical analyses, including but not limited to, analysis of variance, regression, categorical data analysis, multivariate analysis, survival analysis, psychometric analysis, cluster analysis, and nonparametric analysis.

As used herein, the phrase "matriptase profile" means at least one measurement, such as but not limited to a quantity, expression levels, or concentration, taken from a test sample of the subject. Thus a matriptase profile may consist of a single measurement of the active matriptase as provided by the methods of the present invention. A matriptase profile may also comprise a single measurement of the active matriptase as provided by the methods of the present invention in addition to other data that provides information about the status of matriptase activity (or inactivity) in the cell sample. Other such information that may be included in a matriptase profile includes but is not limited to zymography results, antibody binding assays, Western Blots, as well as data related to the status/levels/activity of (HAI)-1, to name a few.

If it is determined that a subject has an increased risk of developing or acquiring a condition marked by the presence of abnormal lymphoid or myeloid cells, the attending health care provider may subsequently prescribe or institute a treatment program. In this manner, the present invention also provides for methods of screening individuals as candidates for treatment of a condition marked by the presence of abnormal lymphoid or myeloid cells. The attending healthcare worker may begin treatment, based on the subject's measured activated matriptase levels or matriptase profile, before there are perceivable, noticeable or measurable signs of a condition marked by the presence of abnormal lymphoid or myeloid cells in the individual.

As discussed above, the present invention also include methods of monitoring the progression of conditions marked by the presence of abnormal lymphoid or myeloid cells, as well as monitoring the progression of the development of abnormal lymphoid cells or abnormal myeloid cells in a subject, with the methods comprising determining the subject's measured activated matriptase levels or matriptase profile more than once over a period of time. For example, some embodiments of the methods of the present invention will comprise determining the subject's measured activated matriptase levels or matriptase profile two, three, four, five, six, seven, eight, nine, 10 or even more times over a period of time, such as a year, two years, three, years, four years, five years, six years, seven years, eight years, nine years or even 10 years or longer. The methods of monitoring a subject's risk of developing a condition marked by the presence of abnormal lymphoid or myeloid cells as well as monitoring the progression or risk of the development of abnormal lymphoid cells or abnormal myeloid cells in a subject would also include embodiments in which the subject's measured activated matriptase levels or matriptase profile are/is assessed during and after treatment of a condition marked by the presence of abnormal lymphoid or myeloid cells. In other words, the present invention also includes methods of monitoring the efficacy of treatment of a condition marked by the presence of abnormal lymphoid or myeloid cells by assessing the subject's measured activated matriptase levels or matriptase profile over the course of the treatment and after the treatment.

Accordingly, the present invention also relates to methods of monitoring the progression of a treatment for abnormal lymphoid cells, abnormal myeloid cells or a condition marked by the presence of abnormal lymphoid cells or abnormal myeloid cells in a subject receiving the treatment. The methods would comprise subjecting at least two separate cell samples, taken from the subject at various time points, to conditions that will activate any inactive matriptase present in the cell sample, and measuring the levels of activated matriptase in each of the cell samples. Once measured, these levels can then be compared to one another to determine if activated matriptase is changing over time. A decline in the levels of activated matriptase over time would be indicative that the treatment for the abnormal lymphoid cells, abnormal myeloid cells or a condition marked by the presence of abnormal lymphoid cells or abnormal myeloid cells is not ineffective, and an increase in the levels of activated matriptase over time would be indicative that the treatment for the abnormal lymphoid cells, abnormal myeloid cells or a condition marked by the presence of abnormal lymphoid cells or abnormal myeloid cells is not effective.

The present invention also relates to kits for determining the presence or absence of abnormal lymphoid cells or abnormal myeloid cells in a cell sample from a subject. The kits of the present invention comprise at least one solution to activate inactive matriptase present in the cell sample and a substrate on which the activated matriptase will act. In one specific embodiment, the solutions of the kits comprise a buffer with an acidic pH. In more specific embodiments, the solutions of the kits comprise acidic phosphate buffer saline and/or other buffers having a mildly acidic pH between pH 5 and pH 6.9. In one embodiment of the methods and kits of the present invention the acidic buffers do not contain chloride or salts containing chloride. In more specific embodiments, the solutions of the kits comprise an acidic buffer with a pH of between about 6.9 and about 5.0. In more specific embodiments, the solutions of the kits comprise an acidic buffer with a pH of between about 6.8 and about 5.2, between about 6.6 and about 5.4, between about 6.4 and about 5.6, between about 6.2 and about 5.8, between about 6.1 and about 5.9, or about 6.0. In even more specific embodiments, the solutions of the kits comprise a phosphate buffer with a pH of between about 6.9 and about 5.0, between about 6.8 and about 5.2, between about 6.6 and about 5.4, between about 6.4 and about 5.6, between about 6.2 and about 5.8, between about 6.1 and about 5.9, or about 6.0.

All patents and publications mentioned in this specification are indicative of the level of those skilled in the art to which the invention pertains. All patents and publications cited herein are incorporated by reference to the same extent as if each individual publication was specifically and individually indicated as having been incorporated by reference in its entirety.

The examples herein are intended to be illustrative of only some of the embodiments of the present invention and are not intended to limit the scope of the invention described herein.

EXAMPLES

Example 1

Venous whole blood (10 mL) was collected in acid citrate dextrose solution A-contained tubes (Becton, Dickinson and Company) from 10 normal females. The samples were stored at 4° C. before processing for the assays. For matriptase assays, 1 mL of whole blood was transferred into sterile tubes and diluted with 1 mL cold PBS alone or with increasing numbers of RPMI 8226 myeloma cells. The diluted blood was carefully layered on to Ficoll-Paque Plus (GE Healthcare) at a blood-to-Ficoll ratio of about 4:3. Centrifugation (1000 rpm, 30 min) was performed to obtain a mononuclear cell fraction that was aspirated and washed in PBS twice with centrifugation. Finally, the cell pellets were resuspended in 2004 of 150 mM phosphate buffer, pH 6.0 and incubated at ambient temperature for about 30 min. The supernatant was then collected by centrifugation for matriptase activity assays.

Matriptase activity was assessed by using the synthetic fluorogenic peptide substrate N-t-Boc-Gln-Ala-Arg-AMC (Enzo Life Science). For the assays, supernatants were neutralized with 2M Trizma-base in the ratio of about 20:1 to pH 7.4 and then mixed with 0.5 mM peptide substrates. The increase in fluorescence resulting from hydrolysis of the peptide substrates was recorded with excitation at 360 nm and emission at 480 nm in a Synergy HT multi-mode microplate reader (Bio-Tek, Winooski, Vt.). The results were plotted with time (min) versus increased fluorescence (RFU) and the enzymatic velocity in RFU/min was calculated.

Example 2

Whole blood was taken from subjects with Chronic Lymphocytic Leukemia (CLL) at various stages of clinical management and peripheral blood lymphocytes (PBLs) were prepared on a Ficoll gradient. A portion of the cells was lysed for the presence of matriptase by Western Blot analysis, after which the remaining cells were subjected to acid-induced activation of the matriptase. Prior to activation, the inactive matriptase is cell-associated. The acid-induced activation of matriptase, however, causes the shedding of the majority of matriptase from the cells. Activity of the matriptase is then assessed by fluorogenic assay as described in Chen, Y., et al., *PLoS One,* 8(5):e62826 (2013), which is incorporated by reference. Table 1 below shows data from the subjects grouped by the stage of clinical management (column 1), matriptase activity determined by the fluorogenic assay in arbitrary units (column 2), a relative estimate of the matriptase protein level in the PBLs prior to acid-induced activation determined by Western Blot assay (column 3), the Lymphocyte # (column 4), the Monocyte # (column 5), and the total White Blood Count (column 6) as determined by clinical assays in blood samples drawn in parallel with the samples for matriptase assay, where these data are available.

TABLE 1

| Pt # | MTP Activity (RFU/min/mL blood) | MTP protein levels | Lymphocyte # | Monocyte # | WBC# |
|---|---|---|---|---|---|
| Naive | | | | | |
| 4 | 361.04 | +++ | 14.7 | 0.6 | 20.4 |
| 5 | 409.98 | +++ | 14.4 | 0.6 | 19.4 |
| 6 | 216.91 | ++ | 7.6 | 0.4 | 12.3 |
| 7 | 630.35 | +++++ | 58.6 | 0.3 | 60.4 |
| 10 | 415.27 | ++ | 20.6 | 0.8 | 26.3 |
| 11 | 186.47 | +++ | 19.8 | 0.7 | 24.5 |
| 15 | 248.95 | +++ | N/A | N/A | 140.4 |
| 16 | 184.77 | +++ | N/A | N/A | 68.6 |
| 20 | 240.42 | ++ | N/A | N/A | N/A |
| Peri-Treatment | | | | | |
| 2 | 1166.64 | +++++ | 45.6 | 1.1 | 49.6 |
| 3 | −5.64 | − | 3.0 | 0.7 | 6.2 |
| 8 | 195.49 | ++ | 18.9 | 1.3 | 23.4 |
| 9 | 150.53 | ++ | 3.3 | 0.6 | 6.1 |
| Post-Treatment | | | | | |
| 12 | 6.28 | − | 1.4 | N/A | 5 |
| 13 | 93.37 | + | N/A | N/A | N/A |
| 17 | 249.67 | ++++ | N/A | N/A | 97 |
| 18 | 64.98 | − | 1.2 | N/A | 10.2 |
| 19 | 52.91 | − | 0.9 | N/A | 5.7 |

What is claimed is:

1. A method of detecting matriptase activity in myeloid cells in a cell sample containing hematopoietic cells, the method comprising
   a) subjecting the cell sample to acidic conditions that will activate any inactive matriptase present in the cell sample,
   b) measuring the level of activated matriptase in the cell sample to determine if the cell sample has elevated levels of activated matriptase over control levels of active matriptase.

2. The method of claim 1, where the measuring of the level of activated matriptase in the cell sample comprises measuring the activity of the activated matriptase.

3. The method of claim 2, wherein measuring the activity of activated matriptase comprises placing a fluorogenic peptide in contact with at least a portion of the cell sample to form a mixture of fluorogenic peptide and cell sample portion, wherein the activated matriptase will act upon the fluorogenic peptide in the mixture and the fluorescence intensity of the mixture will increase after the matriptase acts upon the fluorogenic peptide.

4. The method of claim 3, wherein the fluorogenic peptide is affixed onto a surface.

5. The method of claim 1, where the measuring of the level of activated matriptase in the cell sample comprises measuring the amount of the activated matriptase.

6. The method of claim 1, wherein the cell sample is obtained from a human subject.

7. The method of claim 6, wherein the cell sample is a sample of cells obtained from whole blood from the subject.

8. The method of claim 6, wherein the cell sample is a sample of cells obtained from the bone marrow of the subject.

9. The method of claim 1, wherein activating the matriptase comprises subjecting the cell sample to an acidic buffer.

10. The method of claim 9, wherein the pH of the acidic buffer is between about 6.9 and about 5.0.

11. The method of claim 10, wherein the acidic buffer is phosphate buffer.

12. A method of treating a subject for the presence of abnormal lymphoid cells or abnormal myeloid cells, the method comprising,
   a) subjecting a cell sample taken from the subject to acidic conditions that will activate any inactive matriptase present in the cell sample, said cell sample containing hematopoietic cells,
   b) measuring the level of activated matriptase in the cell sample, and
   c) treating the subject for the presence of abnormal lymphoid cells or abnormal myeloid cells when the sample has elevated levels of activated matriptase over normal levels of activated matriptase.

13. The method of claim 12, where the measuring of the level of activated matriptase in the cell sample comprises measuring the activity of the activated matriptase.

14. The method of claim 13, wherein measuring the activity of activated matriptase comprises placing a fluorogenic peptide in contact with at least a portion of each of the separate cell samples to form a mixture of fluorogenic peptide and cell sample portion, wherein the activated matriptase will act upon the fluorogenic peptide in the mixture and the fluorescence intensity of the mixture will increase after the matriptase acts upon the fluorogenic peptide.

15. The method of claim 14, wherein the fluorogenic peptide is affixed onto a surface.

16. The method of claim 12, where the measuring of the level of activated matriptase in the cell sample comprises measuring the amount of the activated matriptase.

17. The method of claim 12, wherein the cell sample is obtained from a human subject.

18. The method of claim 17, wherein the cell sample is a sample of cells obtained from whole blood from the subject.

19. The method of claim 17, wherein the cell sample is a sample of cells obtained from the bone marrow of the subject.

20. The method of claim 12, wherein activating the matriptase comprises subjecting the cell sample to an acidic buffer.

21. The method of claim 20, wherein the pH of the acidic buffer is between about 6.9 and about 5.0.

22. The method of claim 21, wherein the acidic buffer is phosphate buffer.

23. The method of claim 12, wherein the treatment for abnormal lymphoid cells or abnormal myeloid cells is a treatment for non-Hodgkin lymphoma, Hodgkin lymphoma, leukemia or myeloma.

* * * * *

UNITED STATES PATENT AND TRADEMARK OFFICE
CERTIFICATE OF CORRECTION

PATENT NO. : 10,175,238 B2
APPLICATION NO. : 14/710949
DATED : January 8, 2019
INVENTOR(S) : Chen-Yong Lin, Michael D. Johnson and Feng-Pai Chou It is certified that error appears in the above-identified patent and that said Letters Patent is hereby corrected as shown below:

In the Specification

At Column 1, Lines 6-9, delete the following paragraph:
"Part of the work performed during development of this invention utilized U.S. Government funds under National Institutes of Health Grant No. 1R01CA123223-01A2. The U.S. Government has certain rights in this invention."

And insert in its place the following paragraph:
--This invention was made with government support under grant number CA123223 awarded by the National Institutes of Health. The government has certain rights in the invention.--

Signed and Sealed this
Twelfth Day of December, 2023

Katherine Kelly Vidal
*Director of the United States Patent and Trademark Office*